United States Patent [19]

Balchunis et al.

[11] 4,376,063

[45] Mar. 8, 1983

[54] ANTIMONY HALIDE-ORGANIC PHOSPHONATE ESTER CATIONIC POLYMERIZATION CATALYSTS

[75] Inventors: Robert J. Balchunis, St. Paul; Stephen W. Bany, North St. Paul, both of Minn.

[73] Assignee: Minnesota Mining and Manufacturing Company, St. Paul, Minn.

[21] Appl. No.: 254,974

[22] Filed: Apr. 16, 1981

Related U.S. Application Data

[62] Division of Ser. No. 124,836, Feb. 26, 1980, Pat. No. 4,293,675.

[51] Int. Cl.$^3$ .............................................. B01J 31/22
[52] U.S. Cl. .............................................. 252/429 R
[58] Field of Search ................................... 252/429 R

[56] References Cited

U.S. PATENT DOCUMENTS

| | | | |
|---|---|---|---|
| 3,474,041 | 10/1969 | Kerr | 252/411 |
| 3,590,025 | 6/1971 | Tittle | 252/429 R X |
| 3,652,503 | 3/1972 | Hewertson | 252/429 X |
| 3,707,582 | 12/1972 | Driscoll | 252/429 R X |
| 3,975,299 | 8/1976 | Crathorne et al. | 252/432 |
| 4,003,920 | 1/1977 | Ueeda | 252/435 X |
| 4,013,586 | 3/1977 | Dolan et al. | 252/437 |
| 4,088,822 | 5/1978 | Ogawa et al. | 252/437 X |
| 4,291,145 | 9/1981 | Balchunis et al. | 252/429 R X |

*Primary Examiner*—Patrick Garvin
*Attorney, Agent, or Firm*—Cruzan Alexander; Donald M. Sell; Lorraine R. Sherman

[57] ABSTRACT

The complex formed between a tri-or pentavalent antimony halide and an organic phosphonate ester has been found to be an effective catalyst for cationic polymerization reactions.

3 Claims, No Drawings

ANTIMONY HALIDE-ORGANIC PHOSPHONATE ESTER CATIONIC POLYMERIZATION CATALYSTS

This is a division of application Ser. No. 124,836 filed Feb. 26, 1980 and now U.S. Pat. No. 4,293,675.

BACKGROUND OF THE INVENTION

This invention relates to novel antimony halide-organic phosphonate ester complexes useful as catalysts in organic, cationic polymerization reactions.

The use of catalysts in organic chemistry is well-documented, such catalysts often being specific for one or a limited number of reactions. Antimony-containing acid catalysts have been previously described as useful in hydrocarbon conversion processes, as for example in U.S. Pat. No. 3,975,299.

U.S. Pat. No. 3,590,025 discloses $SbF_5$ and, among other possibilities, fluorides and oxyfluorides of phosphorus as catalysts for the polymerization of tetrafluoroethylene.

The catalysts of U.S. Pat. No. 4,088,822 may contain Pd, P and O and optionally Sb for the simultaneous production of methacrylic acid and methacrylate or acrylic acid and an acrylate. The element Sb is only optionally present in the catalyst composition of patentee's invention, and, in addition, the reaction catalyzed is not a polymerization.

In none of the above catalyst patents does one find antimony halide-organic phosphonate ester compositions.

A number of cations have been combined with phosphorus for catalytic purposes. U.S. Pat. Nos. 3,474,041 and 4,013,586 disclose vanadium, phosphorus, oxygen catalyst systems in the oxidation of hydrocarbons to dicarboxylic acid anhydrides. These compositions are not phosphonate complexes.

Antimony compounds have been disclosed as promoters for other catalysts; i.e. the antimony compounds enhance the activity of the primary catalyst. U.S. Pat. No. 4,003,920 discloses that maleic anhydride can be made by oxidation of unsaturated hydrocarbons in the presence of oxides of tungsten and phosphorus and a catalyst promotor which may, among many other possibilities, be an antimony compound. Patentee does not disclose catalysts useful in cationic polymerizations.

U.S. Pat. No. 3,707,582 discloses $PCl_3$ or $POCl_3$ as a promotor and $SnCl_4$ as a catalyst in the polymerization of isobutene. Patentee states in col. 2, line 27, that $SbCl_5$ is not a useful catalyst in his invention.

The present invention discloses novel compositions of matter that are the reaction product of antimony tri- and pentahalides with organic phosphonates.

Another aspect of the present invention is the disclosure of cationic polymerization catalysts which are antimony halide-organic phosphonate complex compounds.

A further aspect of this invention is to disclose methods of preparation of these novel phosphonate complexes.

An additional aspect of this invention is the disclosure of the use of these novel catalysts in organic cationic polymerization reactions.

It should be noted that the catalysts of the present invention are complexes (which will be discussed below in detail) which appear to be novel in the art. No reference to antimony halide-organic phosphonate ester complexes has been found by the present inventor in the scientific or patent literature.

SUMMARY OF THE INVENTION

The present invention discloses cationic polymerization catalysts which are the reaction product of

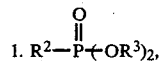

wherein
$R^2$ and $R^3$ are independently selected from
a. phenyl, and
b. alkenyl, halogenated alkyl or alkyl containing one to 18 carbon atoms, and 2. an inorganic tri- or pentavalent antimony compound, said reaction product being a compound which is a complex. The reaction is carried out in a polar organic solvent and yields a catalyst which is effective in cationic polymerizations.

The resultant catalysts,

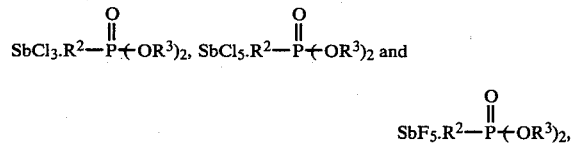

wherein $R^2$ and $R^3$ are as defined above, offer particular advantages over the antimony halide catalysts because the new phosphorus-antimony complexes are less hygroscopic, less hazardous to handle and as catalysts give more controlled rates of reaction.

Polymerization processes may be characterized by the reaction mechanism involved. Thus, homogeneous polymerization reactions may be referred to as free radical, anionic or cationic type polymerizations. These mechanisms of polymerization rely, to a great extent, upon the type of catalyst involved and the formation by the catalyst in solution of a free radical, anion or cation. When chain-reaction polymerizations proceed with cations as the chain-carrying species, the resultant process is known as cationic polymerization. Cationic polymerizations are usually initiated by acids, as for example, Lewis acids, which are defined as electron-pair acceptors. Lewis acids that have been found to be effective cationic polymerization catalysts include: (1) aluminum alkyls that polymerize styrene, butadiene and vinyl ethers (for example $AlEtCl_2$ and $AlEt_2Cl$ are cationic polymerization catalysts used in the preparation of crystalline polyvinyl isobutyl ether), (2) bimetallic compounds such as $(C_5H_5)_2TiCl_2AlClEt$, and (3) trihaloborons.

Antimony pentahalides are very strong Lewis acids that unfortunately have a number of undesirable physical properties which severely limit their use as cationic polymerization catalysts. For example, antimony pentafluoride reacts vigorously with water and acts as a direct fluorinating agent for such compounds as $P_4O_{10}$, $MoCl_5$, $CrO_2Cl_2$ and organochlorine compounds. Hence, $SbF_5$ is extremely reactive and difficult to handle.

Antimony pentachloride readily loses chlorine and the dissociation is appreciable at temperatures even as low as 12° C. $SbCl_5$ is quite hygroscopic, forming a stable monohydrate which is soluble in chloroform. The stable tetrahydrate is insoluble in chloroform. Thus, the pentachloride is also difficult to handle. The pentabromides and iodides are not known as stable compounds. Only SbF$_5$ and SbCl$_5$ are well documented. Mixed halides are known (viz. SbCl$_4$F and SbCl$_2$F$_3$), however and a complex of SbBr$_5$ has been reported (i.e. SbBr$_5$.(C$_2$H$_5$)$_2$O).

The invention described herein consists of antimony-phosphorus compounds with considerably improved physical properties over those of the pure antimony tri- and pentahalides. The new antimony-phosphorus complexes are less-hygroscopic, less reactive liquids or crystalline solids. These complex compounds are effective cationic polymerization catalysts as will be seen subsequently.

A complex is formed between at least two materials when each of those materials is capable of independently existing in a chemically significant environment (e.g., in solution), the isolable complex containing each of those at least two materials with some electronic modification. Thus, the donor (phosphonate) interacts with the acceptor (antimony halide) in such a way as to decrease the electron density on the organic moiety and increase it on the inorganic moiety.

DETAILED DESCRIPTION OF THE INVENTION

The novel catalysts of the present invention are the reaction product of (1) antimony tri- and pentahalides, i.e., SbCl$_3$, SbCl$_5$ and SbF$_5$ with (2) organic phosphonate esters wherein the reaction is carried out in methylene chloride. The phosphonate esters useful in this complex include

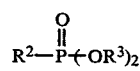

wherein R$^2$ and R$^3$ are independently selected from (1) phenyl, and (2) alkenyl, halogenated alkyl or alkyl of one to 18 carbon atoms. The chemical formulas of the catalyst complexes are

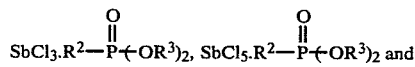

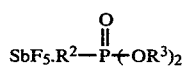

wherein R$^2$ and R$^3$ are as defined above.

The preferred cationic polymerization catalyst is a 1:1 complex of antimony pentachloride and dimethylmethylphosphonate. This is a white solid easily handled without special precautions and it exhibits excellent shelf stability of greater than one year. This catalyst and other phosphonate addition products containing a

functionality are good catalysts. Adducts without the

functionality suffer disadvantages such as instability, handling difficulty or poor catalytic efficiency.

The phosphorus complexes of this invention are formed by combining stoichiometric quantities of a Lewis acid and a Lewis base (See Table 1) in methylene chloride at ambient temperature or below. The complex is then recovered by removing the methylene chloride at reduced pressure.

In the above manner, the following complexes have been synthesized:

TABLE 1

| ACID | BASE $R^2—\overset{O}{\underset{\|}{P}}(OR^3)_2$ | |
|---|---|---|
| | R$^2$ | R$^3$ |
| SbCl$_3$ | CH$_3$ | CH$_3$ |
| SbCl$_5$ | CH$_3$ | CH$_3$ |
| " | CH$_3$CH$_2$ | CH$_2$CH$_3$ |
| " | CH$_2$=CHCH$_2$ | iso-Pr |
| " | CH$_3$ | iso-Pr |
| " | Cl$_3$C | CH$_2$CH$_3$ |
| " | CH$_2$=CHCH$_2$ | CH$_3$ |
| " | C$_{18}$H$_{37}$ | CH$_3$ |
| " | C$_6$H$_5$ | CH$_2$CH$_3$ |
| " | CH$_2$=CH | CH$_2$CH$_3$ |
| " | C$_6$H$_5$ | C$_8$H$_{17}$ |
| SbF$_5$ | CH$_3$ | CH$_3$ |

Changes in physical properties as well as dramatic changes in the IR and proton NMR spectra of these catalytic compounds indicate complex formation. The NMR spectra in particular are indicative of a loss of electron density on the group V heteroatom. Evidence of complex formation is demonstrated by the experimental data of Table 2.

TABLE 2

| PROTON NMR DATA | | |
|---|---|---|
| | Chemical Shifts | |
| | Without SbCl$_5$ | With SbCl$_5$ |
| $\overset{O}{\underset{\|}{CH_3P}}(OCH_3)_2$ b  a | a = 3.79 | 4.12 |
| | b = 1.49 | 2.07 |
| $\overset{O}{\underset{\|}{CH_3CH_2P}}(OCH_2CH_3)_2$ d  b  a  c | a = 4.12 | 4.50 |
| | b = 1.75 | 2.32 |
| | c = 1.34 | 1.50 |
| | d = 1.07 | 1.24 |

NMR spectra were run in CDCl$_3$ (deuterochloroform) solutions of the above compounds. Values are given in δ units downfield from the internal TMS (tetramethylsilane) standard.

Monomers that can be cured or polymerized with the catalyst of this invention, using the latter in a catalytic amount, are those known to undergo cationic polymerization. Useful monomers, which can be polymeric materials, are those containing a hetero oxygen or nitrogen atom attached to one of the carbon atoms of a carbon-carbon double bond (i.e. ethylenic unsaturation), e.g., monomers that contain the structure

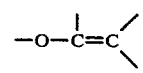

or monomers which polymerize by ring opening of cyclic groups containing hetero O ring atoms.

One general class of useful monomers contain a vinyl group and are typified by vinyl alkyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols such as -hydroxybutyl vinyl ether, and N-vinyl compounds such as N-vinyl-N-methyl octanesulfonamide and N-vinyl-2-pyrrolidinone. A description of vinyl monomers and their use in preparing polymers is set forth in "Vinyl and Related Polymers," by Schildknecht, published by John Wiley & Sons, Inc., New York (1952).

Cationic sensitive monomers which polymerize by ring opening of O-heterocyclic groups and which can be used in the practice of this invention include those which typically contain one or more epoxy groups, which have the structure:

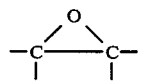

Such monomers, broadly called epoxides, or vicinal epoxides, include epoxy compounds and epoxides of the polymeric type and can be aliphatic, cycloaliphatic, aromatic or heterocyclic and will typically have an epoxy equivalency (i.e., the number of epoxy groups contained in the average molecule) of from 1 to 6, preferably 1 to 3, this value being the average molecular weight of the epoxide divided by the epoxide equivalent weight. Such epoxide monomers are well known and include such epoxides as epichlorohydrins, e.g., epichlorohydrin; alkylene oxides, e.g., propylene oxide, and styrene oxide; alkenyl oxides, e.g., butadiene oxide; glycidyl esters, e.g., ethyl glycidate; gylcidyl-type epoxy resins, e.g., the diglycidyl ethers of Bisphenol A (wherein Bisphenol A is 2,2-bis[4-hydroxyphenyl]propane) and novolak resins, such as described in "Handbook of Epoxy Resins," by Lee and Neville, McGraw-Hill Book Co., New York (1967).

Particularly useful epoxides for this invention are those which contain one or more cyclohexene oxide groups such as the epoxycyclohexanecarboxylates, typified by 3,4-epoxycyclohexylmethyl-3-4-epoxycyclohexanecarboxylate, 3,4-epoxy-2-methylcyclohexylmethyl-3,4-epoxy-2-methylcyclohexanecarboxylate, and bis(3,4-epoxy-6-methylcyclohexylmethyl)adipate. For a more detailed list of useful epoxides of this nature, reference is made to U.S. Pat. No. 3,117,099.

Further epoxides which are particularly useful in the practice of this invention include glycidyl ether monomers of the formula

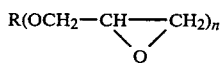

where R is alkyl or phenyl and n is an integer of 1 to 6. An example is the glycidyl ethers of polyhydric phenols obtained by reacting a polyhydric phenol with an excess of chlorohydrin, such as epichlorohydrin, e.g., the diglycidyl ether of Bisphenol A. Further examples of epoxides of this type which can be used in the practice of this invention are described in U.S. Pat. No. 3,018,262.

Other very useful classes of polymerizable epoxy compositions are the epoxy terminated silanes (and precondensates) and epoxysiloxanes. Examples of the epoxy terminated silanes are beta(3,4-epoxycyclohexyl)ethyltrimethoxysilane and gamma(2,3-epoxypropoxy)-propyltrimethoxysilane and their precondensates. Other similar types of compounds useful as monomers are more fully described in U.S. Pat. Nos. 4,049,861, 4,101,513 and 2,946,701. Examples of epoxysiloxanes are represented by the structures,

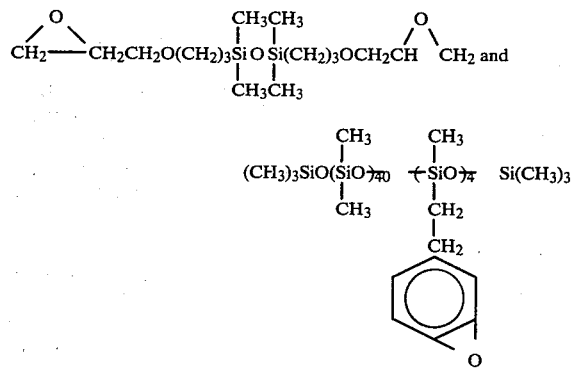

Many other types of epoxysiloxanes which can also contain other groups, e.g. alkyl having 2-18 carbon atoms, attached to the silicon atom are more fully described in Brit. Pat. No. 834,326, U.S. Pat. No. 3,055,774 and assignee's copending patent application, 124,634, filed Dec. 15, 1980, a continuation-in-part of U.S. Ser. No. 124,634, now U.S. Pat. No. 4,313,988.

There are many of commercially available cationic sensitive monomers which can be used in this invention. In particular, epoxies which are readily available include propylene oxide, epichlorohydrin, styrene oxide, vinyl cyclohexene oxide, glycidol, glycidyl methacrylate, phenyl glycidyl ether, 1,2-butane oxide, diglycidyl ether of Bisphenol A, vinylcyclohexene dioxide, 3,4-epoxycyclohexylmethyl-3,4-epoxycyclohexane carboxylate, 3,4-epoxy-6-methylcyclohexylmethyl-3,4-epoxy-6-methylcyclohexane carboxylate, bis(3,4-epoxy-6-methylcyclohexylmethyl)adipate, aliphatic epoxy modified with polypropylene glycol, dipentene dioxide, epoxidized polybutadiene, silicone epoxy, 1,4-butanediol diglycidyl ether, polyglydicyl ether of phenolformaldehyde novolak, resorcinol diglycidyl ether, polyglycol diepoxide, urethane modified epoxide, and polyfunctional flexible epoxides. Information about the commercial sources of these monomers is available in "Handbook of Epoxy Resins," Supra, Appendix 4–2. Another useful class of monomers which can be used are the acetals, such as trioxane.

Preferred cationic sensitive monomers are those of the group consisting of vicinal epoxides, vinyl ethers, N-vinyl compounds, and acetals.

The polymerization or curing of cationic sensitive monomers in the presence of a catalytic effective amount (e.g., 0.1 to 10 weight percent, preferably 0.5 to 4 weight percent based on the weight of monomers) of the catalysts can be carried out by simply mixing the monomeric material with the catalyst and allowing the curing to take place at room temperature or at an elevated temperature (i.e., 50°–150° C.) sufficient to melt the monomer or to accelerate the curing if desired or necessary.

One feature of the compounds of the invention is that they can be used to form solutions of the catalyst and monomer which have latent curing ability. These solutions may have utility in the formation of heat curable coatings and other shaped articles.

Related catalysts are disclosed in assignee's copending patent application, now U.S. Pat. No. 4,291,145, in the names of Robert J. Balchunis and Stephen W. Bany.

The invention is further illustrated by means of the following non-limiting examples.

EXAMPLE 1

Preparation of the Antimony Pentachloride-Dimethylmethylphosphonate Complex (Catalyst A).

In a round bottom flask, under a nitrogen atmosphere, 7.61 g (0.0254 M) of antimony pentachloride was dissolved in 75 ml of methylene chloride. To this yellow solution was added dropwise with stirring a solution of 3.16 g (0.0254 M) of dimethylmethylphosphonate in 20 ml of methylene chloride. The addition was accomplished at a rate such that the exotherm did not become excessive, the temperature being kept below the reflux temperature of methylene chloride (cooling should not be required). By the end of the addition, the initial yellow color had dissipated. The reaction mixture was stirred at ambient temperature for one hour, after which time the solvent was removed by evaporation at reduced pressure. Th crystalline product was thoroughly dried in vacuo (0.1 mm Hg). Analysis calculated for $C_3H_9Cl_5O_3PSb$: % Cl=41.9, observed=42.0%. NMR ($CDCl_3$, TMS): $\delta 4.12$ (d,6H,J=11.6 Hz), 2.08 (d,3H,J=17.6 Hz).

The other complexes of this invention (Table 3) were synthesized in a similar manner.

EXAMPLE 2

To 1 g of the diglycidyl ether of Bisphenol A (Shell Chemical Co., Epon 828) in a glass vial at room temperature was added 0.1 g of a 25% solution of Catalyst A (Example 1) in methylene chloride. The components were mixed thoroughly and the change in physical state observed. After 20 min. a heavy grease was obtained and after two hours the polymer was a glassy solid.

The latency of solutions of the catalyst and Epon 828 and the time to achieve polymerization were also examined. To 10 g of a 10% solution of Epon 828 in methylene chloride was added 0.1 g of a 25% solution of Catalyst A in methylene chloride. No noticeable change in the physical state of the light yellow solution was observed after 24 hr. The solvent was allowed to evaporate from the resultant solution and the residue was heated at 90° C. (1 min) giving a transparent hard brittle polymer.

In contrast to the latter results which provide a solution with latent catalysis capability suitable to provide coatings or other forms which can be heat cured, the addition of 0.1 g of a 25% solution of antimony pentachloride in methylene chloride to 10 g of a 10% solution of Epon 828 in methylene chloride resulted in the immediate formation of a black solid lump precipitate, insoluble in the monomer solution. After 24 hr (with no further change noted), the monomer solution was removed from the black solid, the solvent allowed to evaporate and the residue heated at 90° C. (3 min) giving a viscous fluid, indicating a low degree of polymerization. The hygroscopic complex of antimony pentachloride and methanol also did not provide a solution with latent catalysis capability.

The structures of other complexes of the invention used as polymerization catalysts for Epon 828 are given in Table 3. The procedures, the concentration of catalyst (2.5% by wt. based on the monomer), and the solvent for the catalyst and monomer were the same as those described above. The latency of mixtures or solutions and the time to achieve initial polymerization (gelation) for undiluted (100%) monomer and solutions of the monomer (50% and 10%) in methylene chloride are given. With the exception of Catalyst F and G, use of the catalysts with undiluted monomer resulted in a hard glassy polymer within two hours.

TABLE 3

Polymerization of Epon 828

| Catalyst | Gel Time[a] and Conc. of Monomer Solution | | |
|---|---|---|---|
| | 100% | 50% | 10% |
| B. $SbCl_5 \cdot Cl_3CPO(OEt)_2$ | immediate | immediate | immediate |
| C. $SbCl_5 \cdot C_6H_5PO(OEt)_2$ | 1 min. | 5 min. | 2–3 hr. |
| D. $SbCl_5 \cdot CH_2=CHPO(OEt)_2$ | 30 min. | 45 min. | 5 hr. |
| E. $SbCl_5 \cdot CH_2=CHCH_2PO(OMe)_2$ | 15 min. | 1.5 hr. | 3–4 hr. |
| F. $SbCl_5 \cdot C_{18}H_{37}PO(OME)_2$ | 2 hr. | 4–5 hr. | 24–30 hr. |
| G. $SbCl_5 \cdot MePO(Oiso-Pr)_2$ | 1 hr. | 8–10 hr. | 48 hr. |

[a] the time to achieve a consistency of a heavy grease is recorded.

EXAMPLE 3

The use of Catalyst A (Example 1) to polymerize other monomers is given in Table 4. In each case, 0.1 g of a 25% solution of the catalyst (2.5 wt% catalyst based on the monomer) was mixed with the monomer and the change in physical state was observed.

TABLE 4

Polymerizations with the Dimethylmethylphosphonate Antimony Pentachloride Complexes

| Monomer | Observed ambient exotherm | Observed physical state of cured product | Time to reach observed physical state |
|---|---|---|---|
| vinyl 2-ethylhexyl ether | mild | viscous liquid | 1 hr (25° C.) |
| trioxane | high | powdery solid | 10 sec. (25° C.) |
| N—vinyl-2-pyrrolidinone | none | heavy grease | 2 hr (25° C.) |
| glycidyl methacrylate | none | waxy solid | 2 hr (25° C.) |
| 3,4-epoxycyclohexylmethyl-3,4-epoxycyclohexane-carboxylate | mild | brittle solid | 2 hr (25° C.) |
| epoxypolysiloxane fluid[b] | mild | gummy solid | 1 hr (25°) |
| | " | cheesy solid | 3 min (90° C.) |
| 3-(2,3-epoxypropoxy) propyl-trimethoxysilane | none | cheesy solid | 20 hr. (25° C.) |
| | | cheesy solid | 30 min (90° C.) |
| beta(3,4-epoxycyclohexyl)-ethyltrimethoxysilane | mild | heavy grease | 2 hr. (25° C.) |
| | | cheesy solid | 15 min (90° C.) |

TABLE 4-continued

Polymerizations with the Dimethylmethylphosphonate Antimony Pentachloride Complexes

| Monomer | Observed ambient exotherm | Observed physical state of cured product | Time to reach observed physical state |
|---|---|---|---|
| epichlorohydrin | none | viscous fluid | 30 min (90° C.) |

[b] this fluid (300 cps) was trimethylsiloxy end-blocked and contained an average of about 45 dimethylsiloxane units and four methyl, beta(3,4-epoxycyclohexyl) ethylsiloxane units in the polymer chain. The epoxy equivalent wt. was 1000.

What is claimed is:

1. A catalytic composition of matter for cationic polymerization reactions comprising the 1:1 reaction product complex of
   (a) an inorganic antimony halide compound selected from the class SbCl$_3$, SbCl$_5$ and SbF$_5$, and
   (b) an organic phosphonate ester represented by the formula $$R^2-\overset{\overset{O}{\|}}{P}(OR^3)_2$$

wherein R$^2$ and R$^3$ are independently selected from (1) phenyl, and (2) alkenyl, halogenated alkyl or alkyl of one to 18 carbon atoms, said reaction product complex selected from the class of compounds having the formulas $$SbCl_3 \cdot R^2-\overset{\overset{O}{\|}}{P}(OR^3)_2, \quad SbCl_5 \cdot R^2-\overset{\overset{O}{\|}}{P}(OR^3)_2 \text{ and}$$

$$SbF_5 \cdot R^2-\overset{\overset{O}{\|}}{P}(OR^3)_2,$$

wherein R$^2$ and R$^3$ are as defined above.

2. The composition according to claim 1 wherein the catalytic composition is a 1:1 complex of antimony pentachloride and dimethylmethylphosphonate.

3. A catalytic composition of matter for cationic polymerization reactions comprising the 1:1 reaction product complex of
   (a) an inorganic antimony halide compound selected from the class SbCl$_5$ and SbF$_5$, and
   (b) an organic phosphonate ester represented by the formula $$R^2-\overset{\overset{O}{\|}}{P}(OR^3)_2$$

wherein R$^2$ and R$^3$ are independently selected from (1) phenyl, and (2) alkenyl, halogenated alkyl and alkyl of one to 18 carbon atoms, said reaction product complex selected from the class of compounds having the formulas $$SbCl_5 \cdot R^2-\overset{\overset{O}{\|}}{P}(OR^3)_2$$

and $$SbF_5 \cdot R^2-\overset{\overset{O}{\|}}{P}(OR^3)_2,$$

wherein R$^2$ and R$^3$ are as defined above.

* * * * *